(12) United States Patent
Defay et al.

(10) Patent No.: US 8,667,845 B2
(45) Date of Patent: Mar. 11, 2014

(54) DEVICE AND METHOD FOR DETECTING ELEMENTS IN A FLUID ENVIRONMENT

(75) Inventors: Emmanuel Defay, Voreppe (FR); Marc Aid, Grenoble (FR); Pierre-Patrick Lassagne, Saint-Georges-de-Commiers (FR); Nicolas Sarrut-Rio, Seyssins (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 645 days.

(21) Appl. No.: 12/937,856

(22) PCT Filed: Apr. 14, 2009

(86) PCT No.: PCT/FR2009/000428
§ 371 (c)(1),
(2), (4) Date: Oct. 21, 2010

(87) PCT Pub. No.: WO2009/133301
PCT Pub. Date: Nov. 5, 2009

(65) Prior Publication Data
US 2011/0072901 A1 Mar. 31, 2011

(30) Foreign Application Priority Data
Apr. 14, 2008 (FR) ...................................... 08 02034

(51) Int. Cl.
*G01N 29/036* (2006.01)

(52) U.S. Cl.
USPC ........... 73/592; 73/61.49; 73/61.79; 73/64.53

(58) Field of Classification Search
USPC ............ 73/53.01, 61.41, 61.43–61.45, 61.49, 73/61.71, 61.75, 61.79, 64.53, 579, 592
See application file for complete search history.

(56) References Cited

U.S. PATENT DOCUMENTS

| | | | | |
|---|---|---|---|---|
| 5,076,094 A | * | 12/1991 | Frye et al. | ..................... 73/19.03 |
| 5,189,914 A | * | 3/1993 | White et al. | .................... 73/599 |
| 5,212,988 A | | 5/1993 | White et al. | |
| 5,571,944 A | * | 11/1996 | Pfeifer et al. | ................ 73/24.04 |
| 6,688,158 B2 | * | 2/2004 | Cunningham et al. | ....... 73/24.06 |
| 2006/0213271 A1 | * | 9/2006 | Edmonson et al. | ............. 73/579 |
| 2006/0254356 A1 | * | 11/2006 | Liu et al. | ......................... 73/592 |

OTHER PUBLICATIONS

Laurent et al., "Lamb and shear-horizontal wave production by interdigital transducers deposited on both sides of a piezoelectric plate," *J. Acoust. Soc. Am.*, May 1996, vol. 99, No. 5, pp. 2876-2882.
Laurent et al., "Lamb wave and plate mode in ZnO/silicon and AlN/silicon membrane Application to sensors able to operate in contact with liquid," *Sensors and Actuators*, 2000, vol. 87, pp. 26-37.
Choujaa et al., "AlN/silicon Lamb-wave microsensors for pressure and gravimetric measurements," *Sensors and Actuators* A, 1995, vol. 46-47, pp. 179-182.
International Search Report in International Application No. PCT/FR2009/000428; dated Nov. 16, 2009 (English-language translation).

* cited by examiner

*Primary Examiner* — Daniel S Larkin
(74) *Attorney, Agent, or Firm* — Oliff PLC

(57) ABSTRACT

A device for detecting elements in a fluid environment includes at least one acoustic resonator having a surface designed for fixing of elements. The resonator is configured for generating and measuring Lamb waves fostering generation of symmetrical Lamb waves. The device analyzes the resonance frequency of the resonator to determine the variation of the resonance frequency of the symmetrical Lamb waves representative of the presence of the elements.

10 Claims, 5 Drawing Sheets

DEVICE AND METHOD FOR DETECTING ELEMENTS IN A FLUID ENVIRONMENT

BACKGROUND OF THE INVENTION

The invention relates to a device for detecting elements in a fluid environment comprising:
- at least one acoustic resonator provided with a surface designed for fixing of said elements, said resonator comprising means for generating and measuring Lamb waves enabling both symmetrical Lamb waves to be generated and also signals representative of the resonance frequency of the resonator to be provided; and
- electronic processing means connected to said means for generating and measuring of the resonator.

STATE OF THE ART

In a known manner, detection of elements in an aqueous environment can be performed by using the variation of the resonance frequency of an acoustic resonator. A possible application of these detectors is to observe hybridization of molecules on suitable receptors. An integrated device comprising detectors arranged in parallel, chemical receptors having been deposited on each of which detectors, can be immersed to achieve a collective detection method. This method is a chemical method. When the device is immersed in several different fluid environments, molecules are liable to hybridize on the receptors grafted on each resonator. Should a molecule hybridize, the latter becomes attached to the resonator and modifies the resonance frequency thereof. When they hybridize on the receptors, the elements affect the resonance frequency of the resonator. This frequency modification of the resonator can then be observed by electrical detection.

Such devices conventionally use surface acoustic waves (SAW). To be able to operate, SAW devices have to present an acoustic wave that must not lose energy in water, as an energy loss would in fact greatly reduce the sensitivity of the device. To prevent such an energy loss, the acoustic waves are generated in such a way as to be parallel to the surface in contact with the liquid. Surface acoustic wave devices are well suited in so far as it is possible to generate shear waves which induce a displacement of the waves only in the plane of the resonator. Surface acoustic wave devices do however present the drawback of requiring a piezoelectric substrate, but the silicon used in general for microelectronics is however not a piezoelectric substrate. Production of such devices can therefore not be achieved at low cost by conventional microelectronics methods, in particular on 200 mm diameter substrates.

Another possibility is to use waves called Lamb waves and to manage to prevent the acoustic waves from propagating in the liquid. The Lamb wave is a volume wave which can propagate in a plate, i.e. in a solid medium of very small thickness compared with its lateral dimensions. There are two types of Lamb waves, symmetrical Lamb waves and antisymmetrical Lamb waves. Only antisymmetrical Lamb waves can be sufficiently slow to avoid generating an acoustic wave in the liquid.

The article "Lamb wave and plate mode in ZnO/silicon and AlN/Silicon membrane Application to sensor able to operate in contact with Liquid" by T. Laurent, published in "Sensors and Actuators" Vol. 87 (2000), p 26 to 37, describes such an acoustic resonator used as a mass detector in a non-viscous liquid medium using antisymmetrical Lamb waves. As illustrated in FIGS. 1 to 3, this device comprises a silicon substrate 1, wherein a cavity 2 is formed, covered by a silicon or silicon oxide (SiO2) membrane 3 and by a metallic surface layer 14, this assembly itself being overlaid by a piezo-electric stack 4. Stack 4 comprises a layer of piezoelectric material, for example aluminum nitride or zinc oxide, on which electrodes (not shown in FIG. 1) are deposited. As illustrated in FIG. 2, the device can comprise two interdigitated electrode assemblies, an excitation electrode 5a of the piezoelectric material and a second control electrode 5b forming a delay line. In the alternative embodiment illustrated in FIG. 3, excitation electrode 5a is arranged between two control electrodes 5b. Measurement of the propagation time between excitation electrode 5a and control electrode or electrodes 5b represents the speed of propagation of the acoustic waves in a aqueous medium.

This article illustrates the use of antisymmetrical Lamb waves for the purposes of determining a frequency variation and of thereby achieving a mass measurement. The device thus comprises at least one acoustic resonator provided with a surface designed for fixing of said elements. The resonator comprises means for generating Lamb waves and electrodes designed to provide signals representative of the resonance frequency of the resonator. The measurement electrodes are connected to electronic processing means.

U.S. Pat. No. 5,212,988 describes a device using a transducer coupled to a medium to generate both symmetrical and antisymmetrical Lamb waves in the medium. The transducer can be of one-port type, i.e. it generates and measures the Lamb waves in the medium. Such a device is not optimal, the energy not being maximized in the resonant structure.

OBJECT OF THE INVENTION

The object of the invention consists in providing a device for detecting elements that is easy to produce and to use.

This object is achieved by the fact that the acoustic resonator comprises a piezoelectric stack delimited by two longitudinal lateral surfaces, the means for generating and measuring comprising an odd number of longitudinal upper electrodes, greater than or equal to three, said upper electrodes being uniformly distributed on a top surface of the piezoelectric stack, each longitudinal lateral surface of the piezoelectric stack being aligned with an edge of an associated upper electrode, two adjacent upper electrodes having an opposite polarity, the upper electrodes of the same polarity being electrically connected to one another, at least one lower electrode being arranged on a bottom surface of the piezoelectric stack.

According to one embodiment, the device comprises a single lower electrode having a floating potential and overlaying the whole of the bottom surface of the piezoelectric stack.

According to another embodiment, the device comprises a number of lower electrodes equal to the number of upper electrodes, each lower electrode being arranged facing a corresponding upper electrode, two adjacent lower electrodes having an opposite polarity, the upper and lower electrodes of the same polarity being electrically connected to one another.

According to an alternative embodiment, the upper and lower electrodes facing one another have the same polarity or an opposite polarity.

The invention also relates to a method for detecting elements in a fluid medium by means of a detection device, the method comprising the following successive steps:
- determining a reference resonance frequency corresponding to generation of symmetrical Lamb waves;
- placing the device in said fluid medium;

measuring the resonance frequency of the symmetrical Lamb waves in the fluid medium; and detecting said elements according to the difference between the resonance frequency in the fluid medium and the reference resonance frequency.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF PREFERRED EMBODIMENTS

Figure 1:
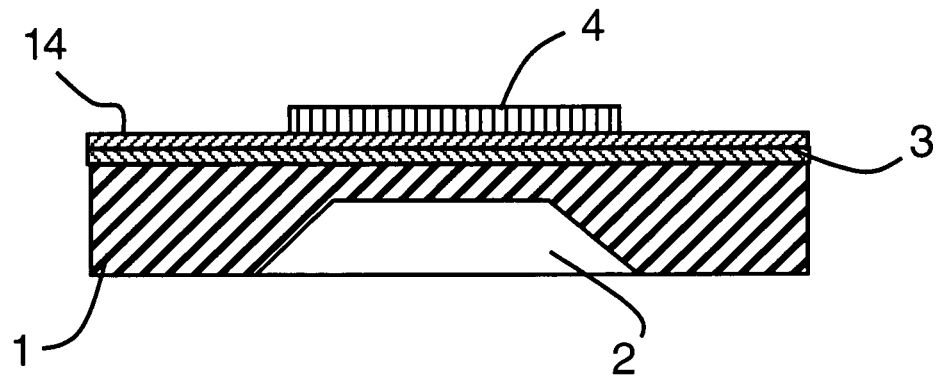
FIGS. 1 to 3 illustrate devices according to the prior art.
Figure 2:
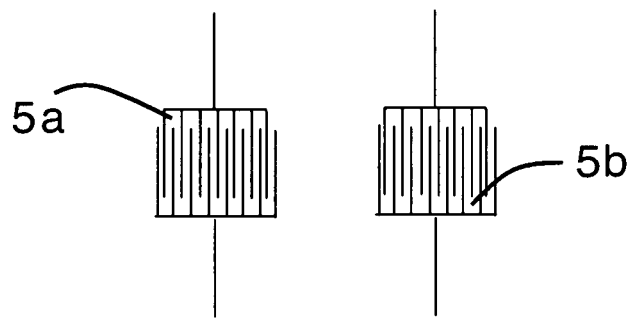
Figure 3:
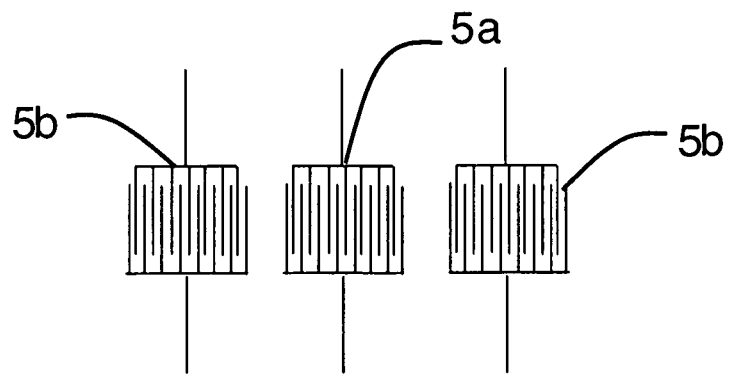
Figure 4:
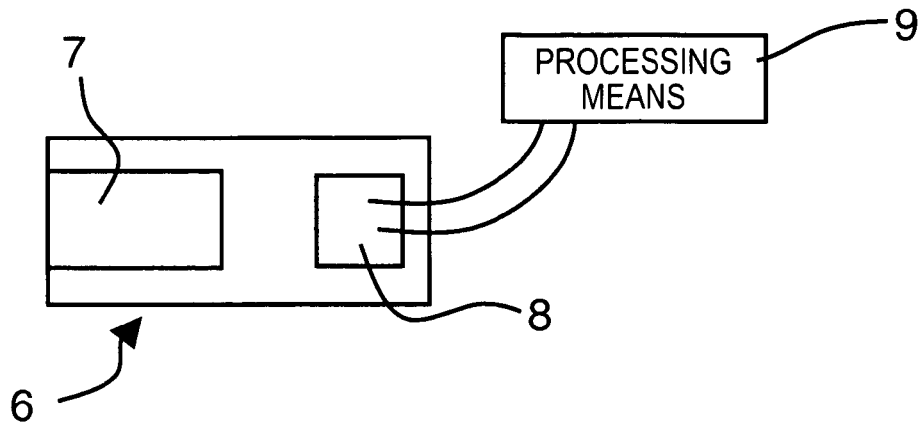
FIG. 4 illustrates a device according to the invention.

As illustrated in FIG. 4, the device for detecting elements in a fluid medium comprises at least one acoustic resonator 6 provided with a surface 7 designed for fixing of the elements to detect their presence. Resonator 6 comprises means for generating and measuring 8 Lamb waves enabling both symmetrical Lamb waves to be generated and signals representative of the resonance frequency of resonator 6 to be provided. Electronic processing means 9 are connected to means for generating and measuring 8 of resonator 6, these electronic processing means 9 enabling interpretation of the signals provided by the means for generating and measuring.

The notion of resonance is to be taken in the broad sense of the word. Indeed, as an anti-resonance is associated with each resonance, the electronic processing means can interpret the resonance or anti-resonance frequency variation. What is meant by resonance is both the resonance proper and the anti-resonance.

To detect an element correctly in a fluid medium, it is important for the device not to generate acoustic waves in the fluid. The acoustic polarization does in fact correspond to displacement of a point of the surface of a vertical and/or horizontal material. It therefore has to be ensured that the resonance frequency of the resonator is lower than the displacement frequency of the acoustic waves in the fluid. This is why antisymmetrical Lamb waves are widely used. It is in fact possible to obtain antisymmetrical Lamb waves at very low frequencies, close to 0 Hz, considerably lower than the displacement frequency of the acoustic waves in the fluid.

The present invention is based on the use of symmetrical Lamb waves. Although these waves are conventionally considered as being parasitic waves inducing a wave in the fluid which disperses the acoustic energy, when they are used correctly, contrary to what is commonly believed, they can be used to detect the presence of elements in a fluid medium. When symmetrical Lamb waves are used in a device enhancing the latter, the resulting acoustic polarization is almost horizontal. The vertical components are only present to a small extent thereby preventing generation of longitudinal acoustic waves in the fluid. The means for generating and measuring 8 Lamb waves are means for fostering generation of symmetrical Lamb waves. Thus, when the device is immersed in a fluid whereas resonator 6 is set to its resonance frequency corresponding to generation of symmetrical Lamb waves, the elements contained in the fluid, which are compatible with surface 7 designed for fixing of said elements, become solidly attached to this surface 7 resulting in a variation of the resonance frequency of the resonator. For this, the acoustic resonator comprises a piezoelectric stack 4 delimited by two longitudinal lateral faces 14a and 14b, and the means for generating and measuring 8 comprise an odd number of longitudinal upper electrodes 5a, 5b, 5c, greater than or equal to three, on a top surface of the piezoelectric stack. Upper electrodes 5a, 5b, 5c are uniformly distributed on top surface 15a of piezoelectric stack 4. Each longitudinal lateral surface 14a, 14b of the stack is aligned with an edge 16 of an associated upper electrode, 5a, 5c in FIG. 5. Two adjacent upper electrodes have an opposite polarity, the electrodes of the same polarity being electrically connected to one another. At least one lower electrode 12 is arranged on a bottom surface of piezoelectric stack 4. The variation is measured by the upper and/or lower electrodes and is then transmitted to electronic processing means 9 to be interpreted.

The method for detecting elements in a fluid medium by means of a detection device, as described in the present text, thus comprises the following successive steps:

determining a reference resonance frequency corresponding to generation of symmetrical Lamb waves at the level of the resonator;

placing the device in said fluid medium in which the presence of certain elements is to be checked;

measuring the resonance frequency of the symmetrical Lamb waves when the device is immersed in the fluid medium; and detecting said elements according to the difference between the resonance frequency in the fluid medium and the reference resonance frequency.

The resonance frequency of the resonator in the fluid medium is measured by the upper and/or lower electrodes and is then interpreted by electronic processing means 9. Electronic processing means 9 determine whether the variation between the resonance frequency in the fluid medium and the reference resonance frequency corresponds to the presence of certain elements in the fluid.

Figure 16:
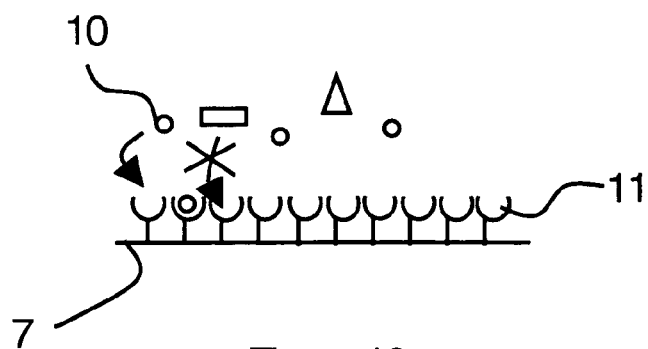
FIG. 16 schematically illustrates hybridization of elements on the resonator.

A hybridization layer can cover a part or all of the resonator so as to form surface 7 designed for fixing the elements. As illustrated in FIG. 16, this layer comprises receptors 11 suitable for certain elements 10, so when the resonator is immersed in the fluid, certain elements 10 can hybridize on receptors 11, hybridization then causing a modification of the mass of the resonator resulting in a variation of the resonance frequency. The receptors are preferably formed on an organic layer overlaying surface 7.

Figure 5:
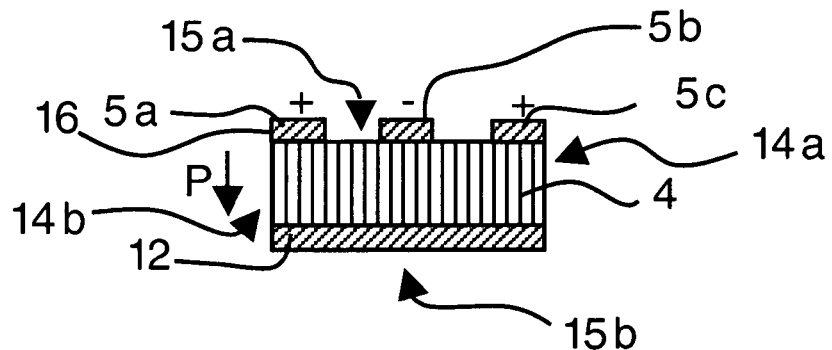
FIGS. 5 and 6, and 8 to 10 illustrate two particular embodiments of a resonator according to the invention.

According to a particular embodiment illustrated in FIG. 5, the acoustic resonator generating symmetrical Lamb waves comprises a piezoelectric stack 4 delimited by two longitudinal lateral surfaces 14a and 14b. The two lateral surfaces 14a and 14b can, as in FIG. 5, be substantially parallel to one another and of the same height so as to connect top surface 15a and bottom surface 15b of piezoelectric stack 4. The means for generating and measuring 8 Lamb waves of the resonator preferably comprise at least three substantially parallel upper electrodes 5a, 5b and 5c arranged on top surface 15a of piezoelectric stack 4. Upper electrodes 5a, 5b, 5c are longitudinal and are arranged in such a way that upper electrodes 5a and 5c each have an edge 16 aligned with an associated lateral surface 14a, 14b. Thus in FIG. 5, the interface of each lateral surface 14a, 14b with top surface 15a forms an arris edge at the level of which upper electrodes 5a, 5c are arranged. A lower electrode 12, at a floating potential, is arranged underneath piezoelectric stack 4 so that bottom surface 15b is totally covered by lower electrode 12. The uniform and therefore symmetrical arrangement of upper electrodes 5a, 5b, 5c with respect to piezoelectric stack 4 associated with an electrode 12 at a floating potential enhances generation of symmetrical Lamb waves in the piezoelectric stack. The stack piezoelectric comprises at least one layer of piezoelectric material.

In FIG. 5, upper electrodes 5a and 5c have the same polarity (+) whereas central upper electrode 5b is of opposite polarity (−) to the polarity of upper electrodes 5a and 5c.

The means for generating symmetrical Lamb waves can comprise means for applying a voltage (+/−) between the upper electrodes of opposite polarity. The upper electrodes of the same polarity are electrically connected to one another.

Figure 6:
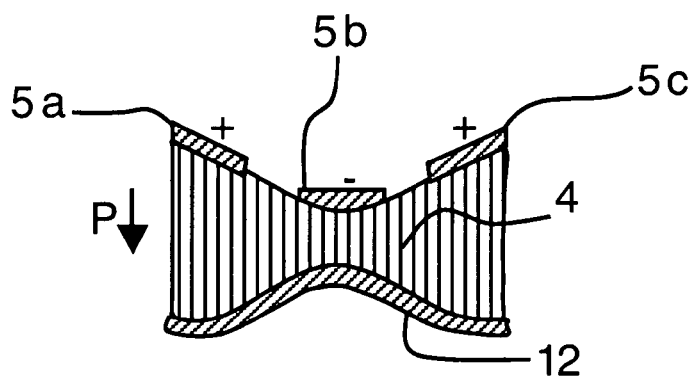
Figure 7:
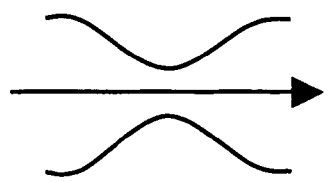
FIG. 7 schematically illustrates displacement of the symmetrical Lamb waves.

In FIG. 6, the structure of the resonator of FIG. 5 deforms according to a profile corresponding substantially to the profile of the symmetrical Lamb waves (FIG. 7) by application of an AC voltage between upper electrodes 5a/5b and 5b/5c at a frequency corresponding to the resonance of a mode of vibration generating symmetrical Lamb waves. This deformation can be explained by a stress field generated in piezoelectric stack 4. In the areas where upper electrodes 5a and 5c are positively polarized with a downward electrical polarization P of the piezoelectric material, the thickness of piezoelectric stack 4 will increase between upper electrode 5a and 5c and electrode 12 at floating potential. In a contrary manner, in the areas where an upper electrode 5b is negatively polarized, piezoelectric stack 4 will tend to reduce its thickness.

The number of upper electrodes is naturally not limited to three, and it is possible to have as many electrodes as desired provided that their number is odd and that two adjacent upper electrodes are of opposite polarity.

Figure 8:
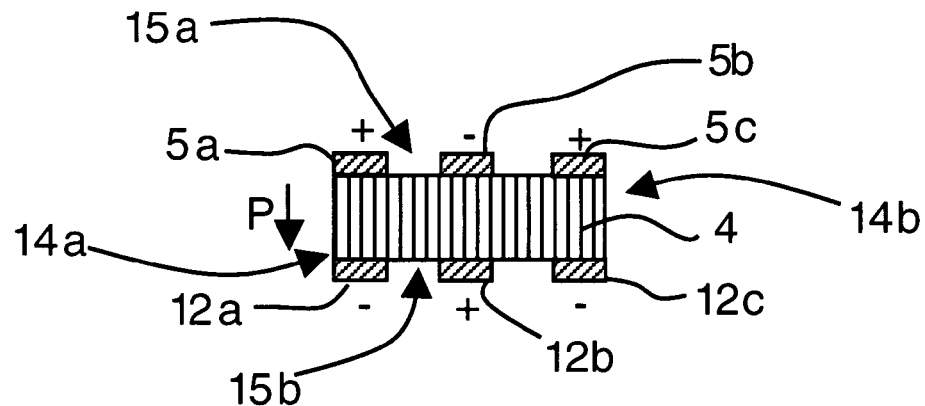
Figure 9:
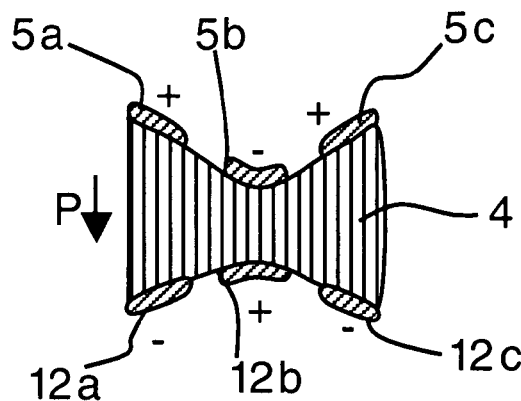

According to another embodiment illustrated in FIG. 8, the means for generating and measuring Lamb waves comprise a plurality of lower electrodes 12a, 12b and 12c each arranged on the bottom surface of the piezoelectric stack facing a corresponding upper electrode 5a, 5b and 5c to form pairs of electrodes 5a/12a, 5b/12b and 5c/12c. Two adjacent lower electrodes are of opposite polarity. The means for generating and measuring symmetrical Lamb waves then comprise means for applying a voltage between the electrodes of a pair of electrodes 5a/12a, 5b/12b and 5c/12c. The upper and lower electrodes of the same polarity are preferably electrically connected to one another. In FIGS. 8 and 9, to foster generation of symmetrical Lamb waves, the facing upper and lower electrodes are of opposite polarity. Thus, in FIG. 8, upper electrodes 5a and 5c have a positive polarity (+) and upper electrode 5b has a negative polarity (−) whereas lower electrodes 12a and 12c have a negative polarity (−) and lower electrode 12b has a positive polarity. Deformation of the resonator (FIG. 9) in the case where piezoelectric stack 4 has a downward electrical polarization P is then obtained on the same principle as before.

Figure 10:
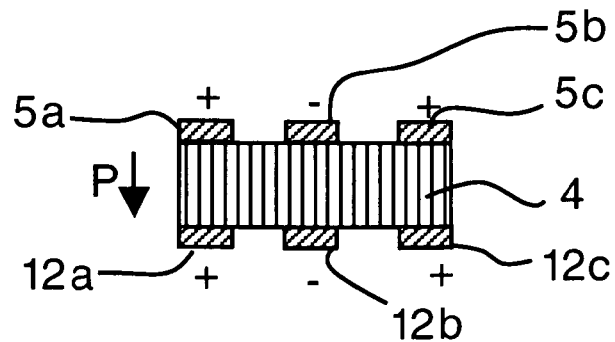

According to an alternative embodiment illustrated in FIG. 10, the device still comprises a number of lower electrodes 12a, 12b, 12c equal to the number of upper electrodes 5a, 5b, 5c, each lower electrode 12a, 12b, 12c being arranged facing a corresponding upper electrode 5a, 5b, 5c. Two adjacent lower electrodes have an opposite polarity and the upper and lower electrodes of same polarity are electrically connected to one another. The facing upper and lower electrodes have the same polarity. Thus, in this figure 10, upper electrodes 5a and 5c and lower electrodes 12a and 12c have a positive polarity (+) whereas upper electrode 5b and lower electrode 12b have a negative polarity (−).

The examples of polarity given above are naturally not restrictive and any type of chaining can be made provided that the polarities of two adjacent electrodes are opposite.

Piezoelectric stack 4 preferably has a thickness of about 10 nm to 5 μm, in particular to give the membrane sufficient rigidity. For example purposes, a piezoelectric material of AlN or Pb(Ze, Ti)O$_3$ (called PZT) or ZnO type can be chosen. This list is naturally not exhaustive.

Figure 11:
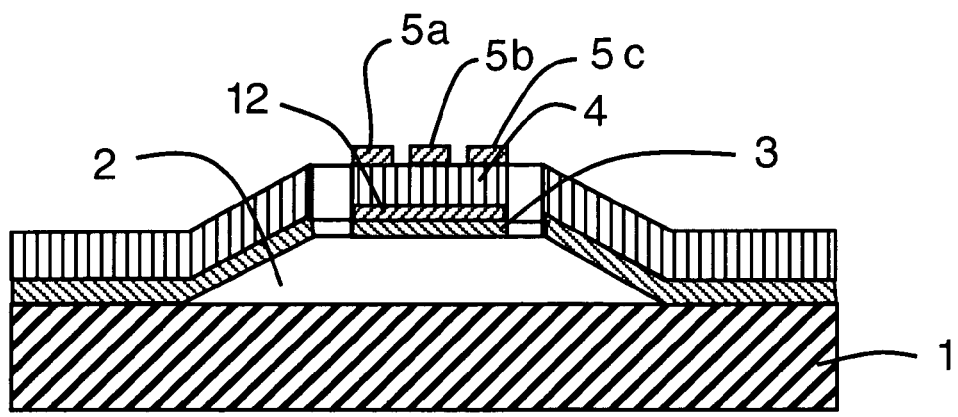
FIGS. 11, 12 and 14 illustrate different implementations of a device according to the invention.
Figure 12:
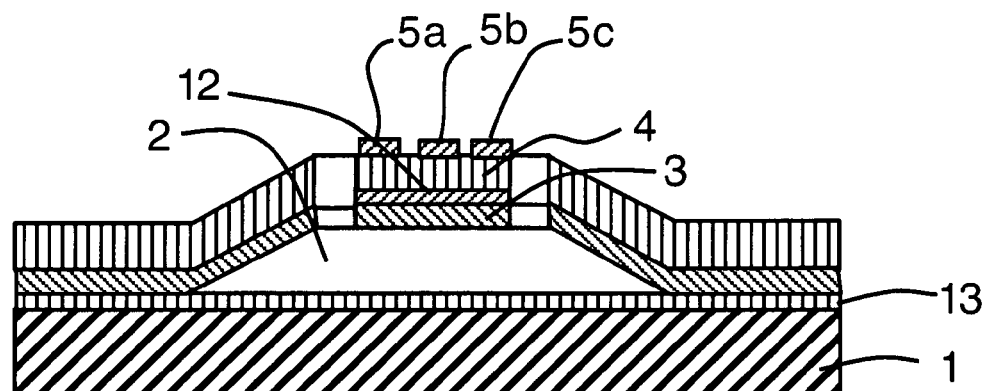
Figure 13:
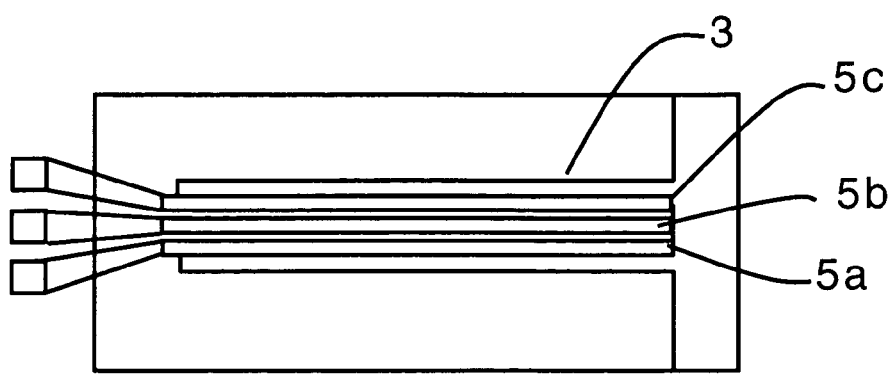
FIG. 13 illustrates a top view of the device according to the invention.

According to a particular embodiment illustrated in FIGS. 11 to 13, the device for detecting elements in a fluid medium comprises a substrate 1. A membrane 3 in the form of a finger, one end whereof is anchored on substrate 1, is made above substrate 1 so as to delineate a cavity 2 between membrane 3 and substrate 1. Prior to releasing the membrane, piezoelectric stack 4 is formed on membrane 3 and comprises at least one layer of piezo-electric material supporting upper electrodes 5a, 5b, 5c arranged on piezo-electric stack 4. Lower electrode or electrodes (12, 12a, 12b, 12c) are arranged between membrane 3 and stack 4. Finally, membrane 3 is released by etching of the sacrificial layer thereby forming cavity 2.

Membrane 3 can also comprise two anchoring points (not shown) on the substrate so as to form a bridge the two ends whereof are anchored on the substrate, the piezoelectric stack being supported by the bridge.

Figure 15:
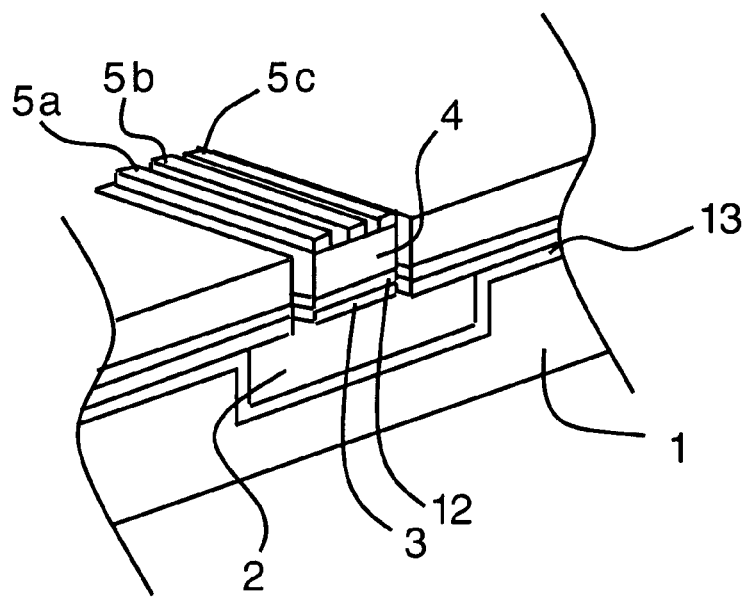
FIG. 15 illustrates a three-dimensional view of the device of FIG. 14.

As illustrated in FIG. 12, the device can be obtained from a silicon substrate 1 on which thermal oxidation is performed to form a silicon oxide layer 13. This layer 13 preferably has a thickness of 0.5 μm. A polymer is then deposited and acts as sacrificial layer subsequently delineating cavity 2 of trapezoid shape. This sacrificial layer preferably has a thickness of 1.5 μm. A layer of silicon nitride designed to form membrane 3 is then deposited, for example by PECVD, on silicon oxide layer 13 and on the sacrificial layer. It preferably has a thickness of 400 nm. A stack is then made comprising lower electrode or electrodes 12, 12a, 12b, 12c, then the layer of piezoelectric material forming stack 4, preferably made from aluminium nitride, and finally upper electrodes 5a, 5b and 5c. Lower electrode or electrodes 12 are produced by sputtering platinum (Pt) to form a layer which can have a thickness of 100 nm, and this layer is then etched by ion etching to form the lower electrode or electrodes before deposition of the piezoelectric material layer. An aluminium nitride layer with a thickness of about 1 μm designed to form the piezoelectric material layer is then sputtered on the whole of the device. A layer with a thickness of about 100 nm designed for formation of upper electrodes 5a, 5b, 5c is then produced by sputtering platinum (Pt) on the aluminium nitride layer forming piezoelectric stack 4. The stack is then etched down to the level of the sacrificial layer so that the piezoelectric stack is delineated by the two lateral surfaces 14a and 14b. This etching of the stack is performed by ion etching of the top layer of platinum forming upper electrodes 5a, 5b, 5c, wet etching for the aluminium nitride layer forming piezoelectric stack 4, and reactive ion etching for the silicon nitride layer forming membrane 3. Finally, the sacrificial layer is removed in an oxygen plasma to form a cavity 2. Membrane 3, lower electrode 12, piezoelectric stack 4 and upper electrodes 5a, 5b, 5c thus form a finger above cavity 2, in a plane perpendicular to FIGS. 11 and 12, to form the resonator as illustrated in FIG. 15.

Figure 14:
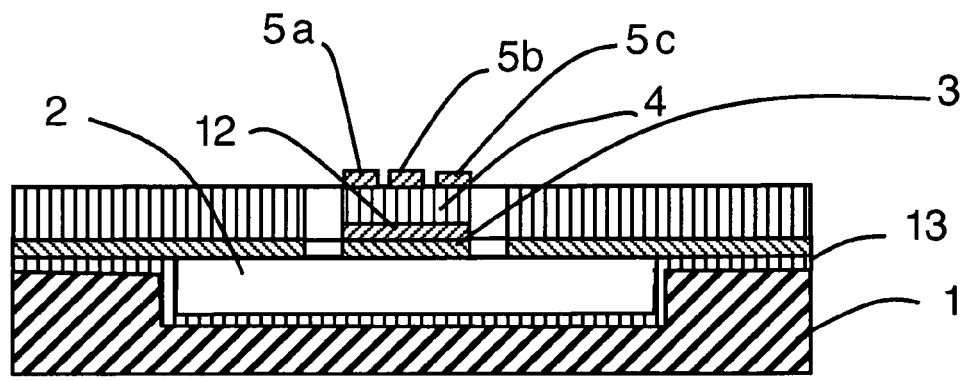

In an alternative embodiment illustrated in FIG. 14, cavity 2 is formed in substrate 1. The latter is for example etched before oxidation so as to form cavity 2. Oxidized layer 13 is then produced and the sacrificial layer is formed by a polymer filling cavity 2. Production of membrane 3 and of the piezoelectric stack, and releasing of membrane 3 by removal of the sacrificial layer are then performed as described in the foregoing (FIG. 15).

To avoid short-circuiting or oxidation of the electrodes, the latter can be covered by an insulator (not shown). The device achieved can thereby be immersed directly in the fluid medium.

The device produced does not present any resonance variation when it is placed in the presence of an aqueous medium. The acoustic waves generated in the aqueous medium are therefore negligible. Furthermore, the device can be used directly in the fluid medium, whereas certain devices first require the structure to be dipped in the fluid medium, evaporation of the water, and only then electrical testing. With this new device, testing can be performed directly in the aqueous medium resulting in a very large time saving.

A plurality of resonators can be produced on a single substrate. Each resonator can then comprise a surface designed for fixing a different type of elements. Each surface is then provided with receptors enabling hybridization of elements, which means that when each resonator is set to its resonance frequency corresponding to generation of symmetrical Lamb waves, the substrate comprising the different resonators can be immersed in the fluid and the electronic processing means are able to analyze the content of the fluid according to the resonance frequency measurements of each resonator.

According to a development of the method for detecting, setting the resonator to its resonance frequency comprises a detection device calibration step. Thus, when the reference frequency is determined, the device is arranged in air or in water. When the acoustic resonator comprises a piezoelectric material, calibration can be performed by making the excitation frequency of the means for generating Lamb waves vary until an impedance peak is measured at the level of the means for generating and measuring, the peak then corresponding to the resonance frequency at which symmetrical Lamb waves are generated in the resonator.

More particularly, the use of a piezoelectric material enables a mechanical stress to be applied to the material by electrical excitation so as to generate symmetrical Lamb waves in the material when the impedance peak is reached. Then, when the resonator is immersed in a fluid, if elements hybridize with the latter, the stress of the piezoelectric material is modified, then implying a variation of the impedance or of the voltage at the terminals of the means for generating and measuring.

The use of a device according to the invention enables the elastic energy in the resonant structure to be maximized, thereby improving the sensitivity of the device.

The invention claimed is:

1. Device for detecting elements in a fluid environment comprising:
    at least one acoustic resonator designed to be disposed in the fluid environment, said at least one acoustic resonator comprising:
        a plate comprising a piezoelectric layer, said plate being delimited by two opposite longitudinal lateral surfaces;
        the piezoelectric layer being delimited by two longitudinal lateral surfaces;
        a surface of the plate designed for fixing of said elements to be detected;
        an odd number of longitudinal upper electrodes, greater than or equal to three, said upper electrodes being uniformly distributed on a top surface of the piezoelectric layer, each longitudinal lateral surface of the piezoelectric layer being aligned along a longitudinal axis with an edge of an associated upper electrode, two adjacent upper electrodes having an opposite polarity, the upper electrodes of the same polarity being electrically connected to one another;
        at least one lower electrode being arranged on a bottom surface of the piezoelectric layer opposite to the top surface of the piezoelectric layer; and
        a generator/detector configured for enabling symmetrical Lamb waves to be generated at a resonance frequency of the acoustic resonator and configured for detecting Lamb waves and providing signals representative of the resonance frequency of the resonator, the generator/detector being electrically coupled to the upper and lower electrodes;
    an electronic processor connected to the detector and configured for determining a variation of the resonance frequency so as to determine presence of said elements.

2. Device according to claim 1, wherein the generator/detector is configured for applying a voltage between the upper electrodes of opposite polarity.

3. Device according to claim 1, comprising a single lower electrode having a floating potential and covering the whole of the bottom surface of the piezoelectric layer.

4. Device according to claim 1, comprising a number of lower electrodes equal to the number of upper electrodes, each lower electrode being arranged facing a corresponding upper electrode, two adjacent lower electrodes having an opposite polarity, the upper and lower electrodes of the same polarity being electrically connected to one another.

5. Device according to claim 4, wherein the facing upper and lower electrodes have the same polarity.

6. Device according to claim 4, wherein the facing upper and lower electrodes have an opposite polarity.

7. Device according to claim 1, wherein the plate has a thickness comprised between 10 nm and 5 µm.

8. Device according to claim 1, wherein receptors to certain elements are placed on the surface of the resonator, immersion of the device in the fluid being intended to achieve hybridization of the corresponding elements with the receptors to bring about a variation of the resonance frequency.

9. Method for detecting elements in a fluid medium by means of a device for detecting according to claim 1 comprising the following successive steps:
    determining a reference resonance frequency corresponding to generation of symmetrical Lamb waves;
    placing the device in said fluid medium;
    measuring the resonance frequency of the symmetrical Lamb waves in the fluid medium; and
    detecting said elements according to the difference between the resonance frequency in the fluid medium and the reference resonance frequency.

10. Method according to claim 9, wherein, when the reference frequency is determined, the device is placed in air or in water.

* * * * *